US006232123B1

(12) United States Patent
Lipp et al.

(10) Patent No.: US 6,232,123 B1
(45) Date of Patent: May 15, 2001

(54) MONOCLONAL ANTIBODIES AGAINST LEUCOCYTE-SPECIFIC G PROTEIN-COUPLED RECEPTORS

(76) Inventors: Martin Lipp, Grussdorfstrasse 15, Berlin-Tegal D-13507 (DE); Reinhold Förster, Wilhelm-Külz -Str. 10, Ahrensfelde D-16356 (DE); Thomas Emrich, Blombergstr. 9, Iffeldorf D-82393 (DE); Ingrid Wolf, 510 4th Ave. W. 308, Seattle, WA (US) 98119; Elisabeth Kremmer, Untere Hauptstr. 28, Freising D-85354 (DE)

( * ) Notice: Subject to any disclaimer, the term of this patent is extended or adjusted under 35 U.S.C. 154(b) by 0 days.

(21) Appl. No.: 08/628,655
(22) PCT Filed: Sep. 22, 1994
(86) PCT No.: PCT/EP94/03175
§ 371 Date: Aug. 13, 1996
§ 102(e) Date: Aug. 13, 1996
(87) PCT Pub. No.: WO95/08576
PCT Pub. Date: Mar. 30, 1995

(30) Foreign Application Priority Data

Sep. 22, 1993 (DE) .................................................. 43 32 256

(51) Int. Cl.[7] ........................ C07K 16/28; A61K 39/395; G01N 33/531
(52) U.S. Cl. .......................... 435/975; 435/7.1; 435/7.23; 435/7.24; 435/7.9; 435/69.1; 435/70.21; 435/70.3; 435/810; 530/388.1; 530/388.22; 424/143.1; 424/144.1; 424/138.1
(58) Field of Search ............................ 530/388.1, 388.22; 435/69.1, 70.21, 70.3, 810, 7.1, 7.23, 7.24, 7.9, 975; 424/143.1, 144.1, 138.1

(56) References Cited

U.S. PATENT DOCUMENTS 5,543,503 * 8/1996 Chanthrapai et al. .......... 530/388.22

FOREIGN PATENT DOCUMENTS

9310814 * 6/1993 (AU) .

OTHER PUBLICATIONS

Dobner et al. (1992) Eur. J. Immunol. 22:2795–99.*
Harlow & Lane (1988) Antibodies, A Laboratory Manual. Cold Spr. Harbor Press.*
Emrich et al., 1994, "Transmembrane Topology of the Lymphocyte–Specific G–Protein–Coupled–Receptor BLR1: Analysis by Flow Cytometry and Immunocytochemistry," *Cellular and Molecular Biology* 40(3):413–419.
Evan et al., 1985, "Isolation of Monoclonal Antibodies Specific for Human c–myc Proto–Oncogene Product," *Mol. and Cell. Biol.* 5:3610–3616.
Förster et al., 1994, "Expression of the G–Protein–Coupled Receptor BLR1 Defines Mature, Recirculating B Cells And A Subset Of T–Helper Memory Cells," *Blood* 84:830–840.
Förster et al., 1993, "A General Method For Screening mAbs Specific For G–Protein Coupled Receptors As Exemplified By Using Epitope Tagged BLR–1–Transfected 293 Cells And Solid Phase Cell ELISA," *Biochem. Biophys. Res. Commun.* 196:1496–1503.
Kearney et al., 1979, "A New Mouse Myeloma Cell Line That Has Lost Immunoglobulin Expression But Permits The Construction of Antibody–Secreting Hybrid Cell Lines," *J. Immunol.* 123:1548–1550.
Köhler and Milstein, 1975, "Continuous Cultures Of Fused Cells Secreting Antibody of Predefined Specificity," *Nature* 256:495–497.
Kozak, 1986, "Point Mutations Define A Sequence Flanking the AUG Initiator Codon That Modulates Translation by Eukaryotic Ribosomes," *Cell* 44:283–292.
Munro and Pelham, 1986, "An Hsp70–like Protein In The ER: Idenity With The 78 kd Glucose–Regulated Protein and Immunoglobin Heavy Chain Binding Protein," *Cell* 46:291–300.
Von Zastrow et al., 1993, "Subtype–specific Differences in the Intracellular Sorting of G Protein–coupled Receptors," *J. Biol. Chem.* 268:763–766.
Von Zastrow and Kobilka, 1992, "Ligand–regulated Internalization And Recycling of Human β2–Adrenergic Receptors Between The Plasma Membrane And Endosomes Containing Transferrin Receptors," *J. Biol. Chem.* 267:3530–3538.
Wolf et al., 1992, "Differentiation–Specific Expression Of A Novel G Protein–Coupled Receptor From Burkitt's Lymphoma," *Biological Chemistry Hoppe–Seyler* 373:840.

* cited by examiner

*Primary Examiner*—Phuong T. Bui
(74) *Attorney, Agent, or Firm*—Pennie & Edmonds LLP

(57) ABSTRACT

The invention relates to monoclonal antibodies against leucocyte-specific G protein-coupled receptors (L-GCR). These antibodies are obtainable by the following steps: (a) introduction of an L-GCR-coding nucleic acid into cells and expression of L-GCR, (b) immunization of an animal with L-GCR-expressing cells of (a), and (c) fusion of spleen cells from the immunized animal of (b) with myeloma cells and production of monoclonal L-GCR antibody-producing hybridoma cells. Furthermore, the invention relates to processes for the production of such antibodies, their use and kits containing the same. In addition, the invention concerns a process for the production of monoclonal GCR antibodies.

10 Claims, 1 Drawing Sheet

MONOCLONAL ANTIBODIES AGAINST LEUCOCYTE-SPECIFIC G PROTEIN-COUPLED RECEPTORS

The invention relates to monoclonal antibodies against leucocyte-specific G protein-coupled receptors, processes for the production thereof and their use as well as kits containing the same. Furthermore, the invention concerns a process for the production of monoclonal antibodies against G protein-coupled receptors.

It is known that receptors play a decisive part in the transduction of signals in an organism. After the binding of the ligands to cell membrane-integrated receptors, the signal is transmitted intracellularly via various mechanisms and processed. There are various families of these receptors, which distinguish themselves by certain structural features. What is called G protein-coupled receptors, internationally abbreviated as GCR (G protein-coupled receptors), are comprised in one family. The G protein is a heterotrimeric GTP-binding protein complex which is composed of the three subunits G-alpha, G-beta and G-gamma. It regulates cellular activities by exchanging GDP by GTP at its alpha-subunit thus activating or inactivating a number of effectors such as adenylyl cyclases, phosphodiesterases, phospholipases and ion channels. Receptors for hormones and neurotransmitters are considered to be representatives of G protein-coupled receptors. They comprise adrenergic and muscarinergic receptors as well as receptors for dopamine, the substance P, thyreotropin, morphine and others.

In addition, there are more and more references to the effect that G protein-coupled receptors are also involved in the regulation of activation, inhibition, migration and cell—cell interaction of immunocompetent cells. It is known that the activation of leucocytes by inflammation mediators such as formyl-MLP, anaphylatoxin C5a, prostaglandins, interleukin-8, MIP-1α and MIP-1β as well as RANTES, also takes place via G protein-coupled receptors. Blocking of these receptors would have an anti-inflammatory effect. However, means for this have not yet been found.

Therefore, it is the object of this invention to provide means by which the leucocyte-specific G protein-coupled receptors can be blocked.

According to the invention this is achieved by providing monoclonal antibodies against leucocyte-specific G protein-coupled receptors (L-GCR). These antibodies are obtainable by the following steps:

(a) introduction of an L-GCR-coding DNA into cells and expression of L-GCR, (b) immunization of an animal with L-GCR-expressing cells of (a), and (c) fusion of spleen cells from the immunized animal of (b) with myeloma cells and production of monoclonal L-GCR antibody-producing hybridoma cells.

The L-GCR-coding nucleic acid may be a DNA, particularly a genome DNA or cDNA. Furthermore, it may be an RNA. The nucleic acids may be provided by conventional methods known from the literature (cf) e.g. Maniatis et al., Molecular Cloning; A Laboratory Manual, Cold Spring Harbor Laboratory (1982); Lipp et al., Eur. J. Immunol. 22 (1992), 2795–2799).

According to the invention, modifications such as additions, deletions and/or substitution of one or more bases, can be introduced into the L-GCR-coding nucleic acid. Additions comprise marker sequences which are fused e.g. to the 5' end or 3' end of L-GCR-coding nucleic acid. Such marker sequences are e.g. codons encoding a protein and protein fragment, respectively, against which a monoclonal antibody exists. The latter serves for detecting the expression of the protein and protein fragment, respectively, and thus also that of L-GCR (cf. von Zastrow and Kobilka, J. Biol. Chem. 267 (1992), 3530-14 3538; von Zastrow et al., J. Biol. Chem. 268 (1993), 763–766; T. Emrich, M. Lipp, not published). Marker sequences can also be inserted in the nucleic acid encoding L-GCR, e.g. in the sequences encoding extracellular or intracellular domains. Further additions are sequences which guarantee a localization of L-GCR in the cell membrane of L-GCR-expressing cells. Such sequences may code for signal peptides, membrane proteins or fragments thereof. They are usually fused to the 5' end of the L-GCR-coding nucleic acid.

According to the invention the L-GCR-coding nucleic acid may exist in an expression unit. It comprises the sequences necessary for the transcription and translation of the L-GCR-coding nucleic acid such as promoter, enhancer, ribosome binding, transcription start and stop as well as translation start and stop sequences. The expression unit may also be present in a vector which may also be a virus. A person skilled in the art knows which sequences of the expression unit are necessary in which arrangement to be able to express L-GCR in certain cells. In addition, the person skilled in the art knows which vectors are suitable for which cells.

According to the invention the L-GCR-coding nucleic acid is introduced into cells to express L-GCR. For this purpose, it is possible to use methods and conditions, known from the literature, for the transfection of cells with nucleic acid. Examples are the calcium phosphate precipitation, DEAE-dextran, electroporation and lipid vesicle methods. It is favorable to use the calcium phosphate precipitation method, about $1-2\times10^6$ cells being transfected with about 15 µg of L-GCR-coding nucleic acid. Eukaryotic and prokaryotic cells may be used as cells. Eukaryotic cells, particularly mammalian cells, e.g. CHO, COS and 293 cells, yeast and insect cells are preferred. The person skilled in the art is familiar with the cells, and they are generally available. The expression of L-GCR can be detected indirectly, e.g. by the detection of the expression of marker sequences, which are comprised by the L-GCR-coding nucleic acid, or by ligand binding. The detection can be made by means of conventional methods known from the literature, e.g. by immunofluorescence, immune enzymology, ELISA technique, flow cytometry and the ligand binding test.

According to the invention an animal is immunized with L-GCR-expressing cells. For this purpose, it is possible to chose conventional conditions known from the literature. It is favorable to give an animal about $3\times10^7$ cells twice, the interval of the administrations being about 28 days. Conventional experimental animals, particularly rats, hamsters, rabbits and mice, may be used as animals. Rats are particularly favorable.

According to the invention spleen cells are taken from the immunized animal. This can be done in usual and known manner. It is favorable to take from the animal spleen cells about 60 hours after the second administration of the antigen. They are then fused with myeloma cells by means of PEG. For this purpose, it is possible to use conventional conditions known from the literature. It is favorable to use as myeloma cells those of the mouse myeloma cell line X63-Ag8.653 (Kearney et al., J. Immunol. 123 (1979), 1548–50), and the ratio of spleen cells to myeloma cells is about 1:3. About 1 week after the fusion, the supernatants of the fused cells are tested for antibody production. For this purpose, it is possible to apply conventional methods known from the literature. It is favorable to carry out flow cytometry. It serves for carrying out comparative measurements of the hybridoma cell supernatants on cells which have been transfected with L-GCR-coding nucleic acid and not modified (untransfected), respectively. Antibody-producing hybridoma cells are then cloned by conventional methods known from the prior art, e.g. by the limiting dilution technique.

Such a hybridoma cell producing the antibody RF8B2 was deposited with the Deutsche Sammlung von Miroorganismen und Zellkulturen [German Type Collection of Microorganisms and Cell Cultures], Mascherodeweg 1b. 38124 Braunschweig, (DSM) under deposit number DSM ACC 2153 on Sep. 8, 1993.

The L-GCR antibodies according to the invention are suitable for diagnostic measures, particularly for determining a patient's immune status. For this purpose, they are labeled e.g. with fluorochromes or biotin and incubated together with other labeled, generally available T cell-specific antibodies and B cell-specific antibodies, respectively, and the patient's body fluids. The portions of T cells, memory T cells, T helper$_1$ cells and T helper$_2$ cells and recirculating non-activated B cells, respectively, are determined. This enables a statement on the patient's immune status. Furthermore, the L-GCR antibody according to the invention can be used to detect diseases, particularly tumors, leukemias, lymphomas, immunodeficiencies and autoimmune diseases.

In addition, the L-GCR antibodies according to the invention are suitable for therapeutic measures. By binding to the receptor, they influence the binding of the physiological ligand or, because of their binding, they themselves activate or inhibit the receptor. The antibodies according to the invention are suitable to inhibit inflammations and to reduce the B and T cell activations. Furthermore, they can influence the migration and interaction of cells. Besides, the antibodies according to the invention—as such or in combination with other antibodies (e.g. against adhesion molecules) or therapeutic agents—are suitable to suppress the formation of tumor metastases. A reduction of the activation of adhesion molecules is effected by inhibiting the ligand binding to L-GCR. This inhibits decisively the formation of tumor metastases.

Furthermore, the antibodies according to the invention can be coupled with known cytotoxins, e.g. ricin, or therapeutic agents, so that degenerated cells can be treated selectively. The binding of the antibodies is followed by the internalization of the receptor complex and thus the effective absorption of the coupled toxin or the therapeutic agents. The above-mentioned antibody RF8B2 is especially suitable for this purpose, since it belongs to subclass IgG$_{2b}$ which is known to have extremely little immunogenicity.

The antibodies according to the invention are manufactured as usual for the administration in therapeutic measures, e.g. as drug.

A kit is also provided according to the invention, which is suitable to carry out the above-mentioned diagnostic measures. Such a kit contains labeled L-GCR antibody, conventional wash buffers and optionally a substrate corresponding to the labeling as well as optionally a further labeled antibody, or labeled L-GCR antibody and labeled T cell-specific antibody and/or B cell-specific antibody as well as conventional wash buffers and optionally a substrate corresponding to the labeling as well as optionally a further labeled antibody.

For the purpose of supplement it is stated that in step (a) of the above-mentioned process for the production of L-GCR antibodies the L-GCR-coding nucleic acid can be replaced by a nucleic acid encoding another G protein-coupled receptor (GCR), e.g. a hormone or neurotransmitter receptor. This then leads to the expression of GCR in cells and furthermore—after immunization of an animal with such cells and fusion of spleen cells of the immunized animal with myeloma cells—to hybridoma cells which produce monoclonal GCR antibodies. According to the invention there is also provided a process which is suitable for the production of monoclonal antibodies against G protein-coupled receptors.

Finally, reference is made to the fact that in place of steps (a) and (b) of the above process for the production of L-GCR antibodies and GCR antibodies, the nucleic acid can be introduced directly into an animal for the expression of L-GCR and GCR, respectively, so as to immunize the animal. In addition, it is possible to use another prior art process for the immortalization of spleen cells in place of the fusion of step (c).

The following examples explain the invention.

EXAMPLE 1

Construction of a plasmid for the expression of L-GCR in eukaryotic cells

The Burkitt's lymphoma receptor 1 (BLR-1) was chosen as an example of a receptor in the L-GCR family. BLR-1 is expressed in Burkitt's lymphoma and lymphatic tissues, but not in other cell lines either of the B cell lineage or of other hematopoietic or non-hematopoietic origin. BLR-1 is a potential candidate involved in the process of physiological trafficking, cell—cell interactions, and activation of mature B lymphocytes in lymphatic tissues. A BLR-1 cDNA (Dobner et al., 1992, *Eur. J. Immunol.*, 22:2795–2799) (SEQ ID NO.:1) was inserted in the restriction sites EcoRI and XbaI of the known and generally available prokaryotic cloning vector pBluescript II KS+, the following modifications having been made beforehand. In the 5' untranslated region, an intercept for the restriction endonuclease EcoRI was inserted 10 base pairs before the translation initiation codon by means of a synthetic oligonucleotide, and the region before the translation initiation codon was modified such that the translation was initiated efficiently (cf. Kozak M., Cell (1986) 44, 283–292). The translation stop codon was removed by means of polymerase chain reaction and the L-GCR-coding DNA was recombined with a synthetic oligonucleotide such that on a protein level the amino acid sequence PGGSGPEQKLISEEDLL (SEQ ID NO:2) was fused to the carboxy terminus of the L-GCR protein. The sequence of the last 11 amino acids originates from the MYC protein and is recognized by the monoclonal antibody 9E10 (cf. Bishop, J. M. et al., Mol. Cell. Biol. 5 (1985), 3610–3616; Munro S., Cell 46 (1986), 291–300) while the first six amino acids serve as spacers to enable unimpeded folding of the MYC epitope. The resulting recombinant DNA was inserted in the restriction sites HindIII and XbaI of the known and generally available eukaryotic expression vector Rc/CMV which enables the expression by means of a heterologous CMV promoter. The plasmid referred to as pBLR1-MYC$_c$ was obtained.

EXAMPLE 2

Expression of L-GCR in eukaryotic cells

The human embryonic kidney tumor cell line 293 (ATCC CRL 1573) was used for the expression of L-GCR in eukaryotes. For this purpose, about 1–2×10$^6$ cells were transfected with 15 µg of plasmid of Example 1 by means of calcium phosphate precipitation technique. The plasmid DNA was previously isolated from the transformed bacteria via ion exchange chromatography. In order to establish stably expressing cell lines, antibiotic-resistant cells of the transfection charge were enriched by the addition of neomycin (200 µg/ml) and positive cell lines were isolated in the expression of the L-GCR-MYC fused protein by limiting cell dilution. The expression of the fused protein was controlled in the case of both transient and stably transfected cells by means of flow cytometry on said cells after permeabilization using the monoclonal antibody 9E10.

EXAMPLE 3

Production of monoclonal antibodies

Immunization of a rat

Female 8-week-old Lou/C rats were immunized with $3\times10^7$ of living L-GCR-transfected 293 cells each. After 28 days, booster was effected with the same amount of immunogen.

Cell fusion 60 hours after the last immunogen administration, the fusion was carried out as usual (cf. e.g. Köhler G. and C. Milstein, Nature 256 (1975), 495–497). In this connection, the spleen of the immunized rat was removed under sterile conditions, ground through a sieve and the collected cells were fused at a ratio of 1:3 with cells of mouse myeloma cell line X63-Ag8.653 (Kearney et al., J. Immunol. 123 (1979) 1548–1550) by means of PEG. One week after the spread in flat bottom plates in HAT selective medium, the colony growth was recorded and the cell culture supernatants of colony-containing recesses were tested for the presence of L-GCR-specific antibodies in the flow cytometer (see below) on stable L-GCR-expressing 293 cells and normal 293 cells by way of comparison. Only those antibodies which had bound to transfected cells but not to normal 293 cells were cloned according to the limiting dilution technique, further proliferated, tested on transiently transfected 293 cells and finally on peripheral leucocytes.

Flow cytometry

The presence of L-GCR antibodies was tested by means of flow cytometry. Comparative measurements with L-GCR-transfected and unchanged 293 cells were carried out as test system. 25 µg of hybridoma cell supernatant each were incubated with 25 µl of the respective cell suspension ($1\times10^7$/ml) at room temperature for 25 min. After washing them in PBS (4% FCS, 4 mM EDTA), the cells were admixed with a 1:160 dilution of a polyclonal goat anti-rat-FITC conjugate. After incubation for 25 minutes and subsequent washing, a specific binding was detected by means of a FACScan flow cytometer. 5000 cells were measured per sample and the fluorescence intensity of the cell population was analyzed. Antibodies which bind specifically to L-GCR could be identified by a comparison between the fluorescence intensity of transfected and unchanged 293 cells Studies on the binding of antibody RF8B2 according to the invention

BRIEF DESCRIPTION OF DRAWINGS

The above-mentioned 293 cells were transfected with L-GCR-coding DNA as usual and not transfected, respectively. The latter cells were referred to as mock-transfected. Antibody RF8B2 according to the invention was labeled as usual using biotin and added to the cells. It showed that RF8B2 binds to transfected 293 cells but not to mock-transfected cells (FIG. 1).

In addition peripheral leucocytes of the blood were purified via Ficoll and stained with the T cell-specific antibody CD4-FITC (FIG. 2) or CD8-FITC (FIG. 3) and with the B cell-specific antibody CD19-FITC (FIG. 4), respectively. Then, the biotin-labeled antibody RF8B2 was added. It showed that 100% of B cells (CD19 positive) (FIG. 4) bind this antibody. In contrast thereto, RF8B2 is bound only by about 14% of the T helper cells (CD4positive) (FIG. 2) and about 2% of the cytotoxic T cells (CD8 positive) (FIG. 3) (FIGS. 2, 3 and 4). This shows the usability of RF8B2 for indicating a differently extensive expression of L-GCR.

Preparation and purification of antibodies

Figure 1:
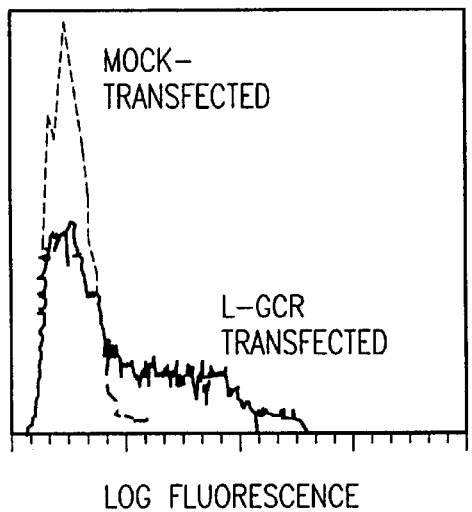
Figure 2:
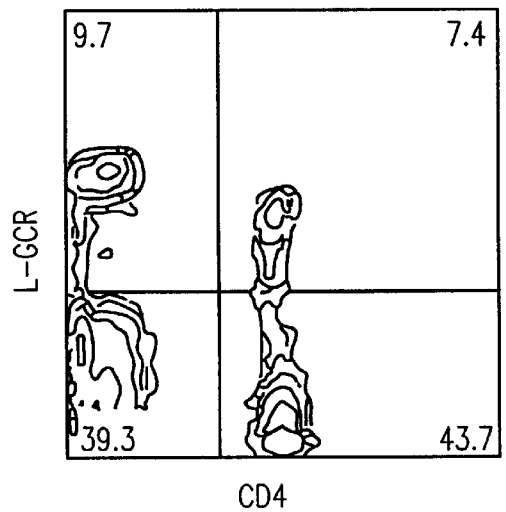
Figure 3:
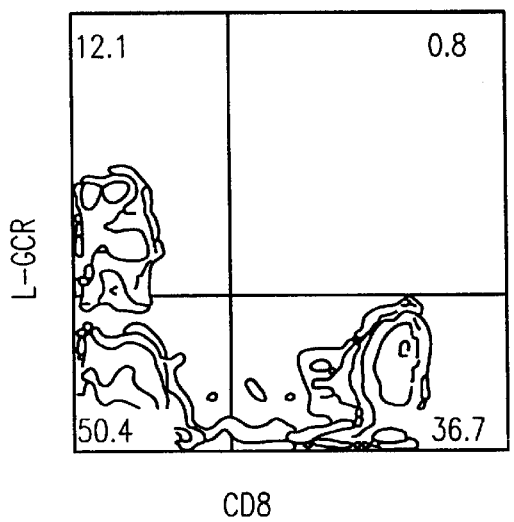
Figure 4:
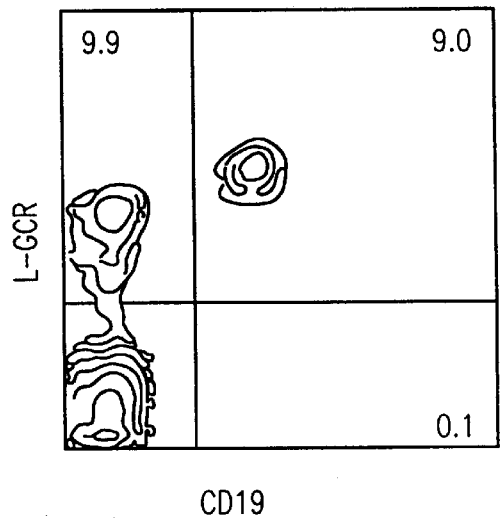

| sample buffer | pH 7.4 | PBS |
|---|---|---|
| elution buffer | pH 2.5 | 0.05 M glycine |
| | | 0.05 M NaCl |
| tenfold Tris-HCl buffer | pH 8.6 | 0.5 M Tris |
| | | 1.5 M NaCl |

The hybridoma cells were proliferated in RPM1 using 10% IgG-free FCS, divided 1:3 every 2 to 3 days and the cell culture supernatant was collected. Protein G affinity chromatography was used to separate the monoclonal antibodies from the cell culture supernatant (cf. Björck and Kronvall, J. Immunol. 132 (1984) 969–974). For this purpose, 1 g of protein G sepharose 4 fast flow was packed in a chromatographic column after swelling and equilibrated using PBS. 200 ml of the supernatant to be purified were applied to the column after microfiltration. A change from PBS to elution buffer released the antibodies bound to sepharose. The eluate fractions corresponding to the extinction peak were dialyzed with PBS.

Labeling of antibodies

| Biotin labeling: | | |
|---|---|---|
| coupling buffer | pH 7.4 | PBS |
| biotin preparation | NHS-LC biotin | |

Here, the coupling was carried out with modification as described (cf. e.g. Peters et al., Monoklonale Antikörper, Herstellung and Charakterisierung [Monoclonal Antibodies, Production and Characterization], Springer Verlag, Berlin (1985)). Protein G-purified eluates were adjusted to 2 mg/ml and dialyzed with coupling buffer for 24 hours. 50 µl of biotin solution (8 mg of biotin in 1 ml DMF) were added to 1.0 ml of MAk solution for the purpose of reaction and incubated at room temperature for 90 min. After the dialysis with PBS and sterile centrifugation, the conjugates were stored at −20° C.

| FITC conjugates | | |
|---|---|---|
| coupling buffer | pH 9.5 | 0.1 M NaHCO$_3$ |

FTIC preparation fluorescein isothiocyanate, protein G-purified eluates were adjusted to 2 mg/ml and admixed with ⅒ vol. of tenfold coupling buffer. For the purpose of reaction, 60 µl of FITC solution (1 mg FITC in 1 ml of coupling buffer) were added to 1.0 ml of mAk solution and incubated at 4° C. overnight. After dialysis with PBS and sterile centrifugation, the conjugate were stored at −20 C.

What is claimed is:

1. A monoclonal antibody against Burkitt's lymphoma receptor 1 (BLR-1), wherein said antibody is produced by a hybridoma cell line which was deposited with the Deutsche Sammlung von Mikroorganismen und Zellkulturen (German Type Collection of Microorganisms and Cell Cultures) (DSM) under deposit number DSM ACC 2153.

2. A kit comprising:
   (a) the BLR-1 antibody according to claim 1, wherein said antibody is labeled; and
   (b) conventional wash buffers.

3. The kit according to claim 2, wherein said label requires a substrate for detection and wherein said kit further comprises a substrate for detecting the label on the antibody.

4. The kit according to claim 3, further comprising a second labeled antibody.

5. The kit according to claim 2, further comprising at least one additional antibody selected from the group consisting of T-cell-specific antibody, B-cell-specific antibody, and T-cell-specific antibody and B-cell-specific antibody.

6. The kit according to claim 5, wherein said label requires a substrate for detection and wherein said kit further comprises a substrate for detecting the label on the antibody.

7. The kit according to claim 6, further comprising at least one additional labeled antibody.

8. The antibody according to claim 1, wherein the antibody is labeled.

9. The labeled antibody according to claim 8, wherein the label on the antibody is selected from the group consisting of a fluorochrome and biotin.

10. The labeled antibody according to claim 9, wherein the fluorochrome label is fluorescein isothiocyanate (FITC).

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 2818 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: Coding Sequence
      (B) LOCATION: 85...1200
      (D) OTHER INFORMATION:

(xi) SEQUENCE DESCRIPTION: SEQ ID NO:1:

```
GCTGCCACCT CTCTAGAGGC ACCTGGCGGG GAGCCTCTCA ACATAAGACA GTGACCAGTC         60

TGGTGACTCA CAGCCGGCAC AGCC ATG AAC TAC CCG CTA ACG CTG GAA ATG          111
                          Met Asn Tyr Pro Leu Thr Leu Glu Met
                            1               5

GAC CTC GAG AAC CTG GAG GAC CTG TTC TGG GAA CTG GAC AGA TTG GAC         159
Asp Leu Glu Asn Leu Glu Asp Leu Phe Trp Glu Leu Asp Arg Leu Asp
 10              15                  20                  25

AAC TAT AAC GAC ACC TCC CTG GTG GAA AAT CAT CTC TGC CCT GCC ACA         207
Asn Tyr Asn Asp Thr Ser Leu Val Glu Asn His Leu Cys Pro Ala Thr
                 30                  35                  40

GAG GGT CCC CTC ATG GCC TCC TTC AAG GCC GTG TTC GTG CCC GTG GCC         255
Glu Gly Pro Leu Met Ala Ser Phe Lys Ala Val Phe Val Pro Val Ala
             45                  50                  55

TAC AGC CTC ATC TTC CTC CTG GGC GTG ATC GGC AAC GTC CTG GTG CTG         303
Tyr Ser Leu Ile Phe Leu Leu Gly Val Ile Gly Asn Val Leu Val Leu
             60                  65                  70

GTG ATC CTG GAG CGG CAC CGG CAG ACA CGC AGT TCC ACG GAG ACC TTC         351
Val Ile Leu Glu Arg His Arg Gln Thr Arg Ser Ser Thr Glu Thr Phe
 75                  80                  85

CTG TTC CAC CTG GCC GTG GCC GAC CTC CTG CTG GTC TTC ATC TTG CCC         399
Leu Phe His Leu Ala Val Ala Asp Leu Leu Leu Val Phe Ile Leu Pro
 90                  95                 100                 105

TTT GCC GTG GCC GAG GGC TCT GTG GGC TGG GTC CTG GGG ACC TTC CTC         447
Phe Ala Val Ala Glu Gly Ser Val Gly Trp Val Leu Gly Thr Phe Leu
                110                 115                 120

TGC AAA ACT GTG ATT GCC CTG CAC AAA GTC AAC TTC TAC TGC AGC AGC         495
Cys Lys Thr Val Ile Ala Leu His Lys Val Asn Phe Tyr Cys Ser Ser
                125                 130                 135

CTG CTC CTG GCC TGC ATC GCC GTG GAC CGC TAC CTG GCC ATT GTC CAC         543
```

```
                                                         -continued

Leu Leu Leu Ala Cys Ile Ala Val Asp Arg Tyr Leu Ala Ile Val His
        140                 145                 150

GCC GTC CAT GCC TAC CGC CAC CGC CGC CTC CTC TCC ATC CAC ATC ACC       591
Ala Val His Ala Tyr Arg His Arg Arg Leu Leu Ser Ile His Ile Thr
        155                 160                 165

TGT GGG ACC ATC TGG CTG GTG GGC TTC CTC CTT GCC TTG CCA GAG ATT       639
Cys Gly Thr Ile Trp Leu Val Gly Phe Leu Leu Ala Leu Pro Glu Ile
170                 175                 180                 185

CTC TTC GCC AAA GTC AGC CAA GGC CAT CAC AAC AAC TCC CTG CCA CGT       687
Leu Phe Ala Lys Val Ser Gln Gly His His Asn Asn Ser Leu Pro Arg
                190                 195                 200

TGC ACC TTC TCC CAA GAG AAC CAA GCA GAA ACG CAT GCC TGG TTC ACC       735
Cys Thr Phe Ser Gln Glu Asn Gln Ala Glu Thr His Ala Trp Phe Thr
            205                 210                 215

TCC CGA TTC CTC TAC CAT GTG GCG GGA TTC CTG CTG CCC ATG CTG GTG       783
Ser Arg Phe Leu Tyr His Val Ala Gly Phe Leu Leu Pro Met Leu Val
        220                 225                 230

ATG GGC TGG TGC TAC GTG GGG GTA GTG CAC AGG TTG CGC CAG GCC CAG       831
Met Gly Trp Cys Tyr Val Gly Val Val His Arg Leu Arg Gln Ala Gln
    235                 240                 245

CGG CGC CCT CAG CGG CAG AAG GCA GTC AGG GTG GCC ATC CTG GTG ACA       879
Arg Arg Pro Gln Arg Gln Lys Ala Val Arg Val Ala Ile Leu Val Thr
250                 255                 260                 265

AGC ATC TTC TTC CTC TGC TGG TCA CCC TAC CAC ATC GTC ATC TTC CTG       927
Ser Ile Phe Phe Leu Cys Trp Ser Pro Tyr His Ile Val Ile Phe Leu
                270                 275                 280

GAC ACC CTG GCG AGG CTG AAG GCC GTG GAC AAT ACC TGC AAG CTG AAT       975
Asp Thr Leu Ala Arg Leu Lys Ala Val Asp Asn Thr Cys Lys Leu Asn
            285                 290                 295

GGC TCT CTC CCC GTG GCC ATC ACC ATG TGT GAG TTC CTG GGC CTG GCC      1023
Gly Ser Leu Pro Val Ala Ile Thr Met Cys Glu Phe Leu Gly Leu Ala
        300                 305                 310

CAC TGC TGC CTC AAC CCC ATG CTC TAC ACT TTC GCC GGC GTG AAG TTC      1071
His Cys Cys Leu Asn Pro Met Leu Tyr Thr Phe Ala Gly Val Lys Phe
    315                 320                 325

CGC AGT GAC CTG TCG CGG CTC CTG ACC AAG CTG GGC TGT ACC GGC CCT      1119
Arg Ser Asp Leu Ser Arg Leu Leu Thr Lys Leu Gly Cys Thr Gly Pro
330                 335                 340                 345

GCC TCC CTG TGC CAG CTC TTC CCT AGC TGG CGC AGG AGC AGT CTC TCT      1167
Ala Ser Leu Cys Gln Leu Phe Pro Ser Trp Arg Arg Ser Ser Leu Ser
                350                 355                 360

GAG TCA GAG AAT GCC ACC TCT CTC ACC ACG TTC TAGGTCCCAG TGTCCCCTTT    1220
Glu Ser Glu Asn Ala Thr Ser Leu Thr Thr Phe
            365                 370

TATTGCTGCT TTTCCTTGGG GCAGGCAGTG ATGCTGGATG CTCCTTCCAA CAGGAGCTGG    1280

GATCCTAAGG GCTCACCGTG GCTAAGAGTG TCCTAGGAGT ATCCTCATTT GGGGTAGCTA    1340

GAGGAACCAA CCCCATTTCT AGAACATCCC TGCCAGCTCT TCTGCCGGCC CTGGGGCTAG    1400

GCTGGAGCCC AGGGAGCGGA AAGCAGCTCG AAGGCACAGT GAAGGCTGTC CTTACCCATC    1460

TGCACCCCCC TGGGCTGAGA GAACCTCACG CACCTCCCAT CCTAATCATC CAATGCTCAA    1520

GAAACAACTT CTACTTCTGC CCTTGCCAAC GGAGAGCGCC TGCCCCTCCC AGAACACACT    1580

CCATCAGCTT AGGGGCTGCT GACCTCCACA GCTTCCCCTC TCTCCTCCTG CCCACCTGTC    1640

AAACAAAGCC AGAAGCTGAG CACCAGGGGA TGAGTGGAGG TTAAGGCTGA GGAAAGGCCA    1700

GCTGGCAGCA GAGTGTGGCT TCGGACAACT CAGTCCCTAA AAACACAGAC ATTCTGCCAG    1760

GCCCCCAAGC CTGCAGTCAT CTTGACCAAG CAGGAAGCTC AGACTGGTTG AGTTCAGGTA    1820
```

-continued

```
GCTGCCCCTG GCTCTGACCG AAACAGCGCT GGGTCCACCC CATGTCACCG GATCCTGGGT      1880

GGTCTGCAGG CAGGGCTGAC TCTAGGTGCC CTTGGAGGCC AGCCAGTGAC CTGAGGAAGC      1940

GTGAAGGCCG AGAAGCAAGA AAGAAACCCG ACAGAGGGAA GAAAAGAGCT TTCTTCCCGA      2000

ACCCCAAGGA GGGAGATGGA TCAATCAAAC CCGGCTGTCC CCTCCGCCCA GGCGAGATGG      2060

GGTGGGGGGA GAACTCCTAG GGTGGCTGGG TCCAGGGGAT GGGAGGTTGT GGGCATTGAT      2120

GGGGAAGGAG GCTGGCTTGT CCCCTCCTCA CTCCCTTCCC ATAAGCTATA GACCCGAGGA      2180

AACTCAGAGT CGGAACGGAG AAAGGTGGAC TGGAAGGGGC CCGTGGGAGT CATCTCAACC      2240

ATCCCCTCCG TTGGCATCAC CTTAGGCAGG GAAGTGTAAG AAACACACTG AGGCAGGAAC      2300

TCCCAGGCCC AGGAAGCCGT GCCCTGCCCC CGTGAGGATG TCACTCAGAT GGAACCGCAG      2360

GAAGCTGCTC CGTGCTTGTT TGCTCACCTG GGGTGTGGGA GGCCCGTCCG GCAGTTCTGG      2420

GTGCTCCCTA CCACCTCCCC AGCCTTTGAT CAGGTGGGGA GTCAGGGACC CCTGCCCTTG      2480

TCCCACTCAA GCCAAGCAGC CAAGCTCCTT GGGAGGCCCC ACTGGGGAAA TAACAGCTGT      2540

GGCTCACGTG AGAGTGTCTT CACGGCAGGA CAACGAGAAA GCCCTAAGAC GTCCCTTTTT      2600

TCTCTGAGTA TCTCCTCGCA AGCTGGGTAA TCGATGGGGA GTCTGAAGCA GATGCAAAGA      2660

GGCAGAGGAT GGATTTTGAA TTTTCTTTTT AATAAAAAGG CACCTATAAA ACAGGTCAAT      2720

ACAGTACAGG CAGCACAGAG ACCCCCGGAA CAAGCCTAAA AATTGTTTCA AAATAAAAAC      2780

CAAGAAGATG TCTTCAAAAA AAAAAAAAAA AAAAAAAA                              2818
```

(2) INFORMATION FOR SEQ ID NO:2:

(i) SEQUENCE CHARACTERISTICS:
        (A) LENGTH: 17 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Pro Gly Gly Ser Gly Pro Glu Gln Lys Leu Ile Ser Glu Glu Asp Leu
1               5                   10                  15
Leu
```